(12) United States Patent
Green et al.

(10) Patent No.: US 6,332,886 B1
(45) Date of Patent: Dec. 25, 2001

(54) SURGICAL REAMER AND METHOD OF USING SAME

(75) Inventors: James M. Green, Portland, OR (US); Alexandre N. Perrier, Basel (CH); Stanley J. Kmiec, Jr., Coopersburg, PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/495,932

(22) Filed: Feb. 2, 2000

Related U.S. Application Data

(60) Provisional application No. 60/118,485, filed on Feb. 3, 1999.

(51) Int. Cl.[7] .................................................. A61B 17/16
(52) U.S. Cl. ............................................. 606/80; 606/79
(58) Field of Search ........................................ 606/79–82

(56) References Cited

U.S. PATENT DOCUMENTS

| | | | |
|---|---|---|---|
| 3,528,425 | 9/1970 | Banko | 128/305 |
| 3,584,629 | 6/1971 | Hoef et al. | 128/305 |
| 3,732,858 | 5/1973 | Banko | 128/2 B |
| 3,976,077 | 8/1976 | Kerfoot, Jr. | 128/305 |
| 4,445,509 | 5/1984 | Auth | 128/305 |
| 4,553,957 | 11/1985 | Williams et al. | 604/43 |
| 4,573,979 | 3/1986 | Blake | 604/240 |
| 4,646,738 | 3/1987 | Trott | 128/305 |
| 4,649,919 | 3/1987 | Thimsen et al. | 128/305 |
| 4,735,604 | 4/1988 | Watmough et al. | 604/22 |
| 4,751,922 | 6/1988 | DiPietropolo | 128/92 |
| 4,811,734 | 3/1989 | McGurk-Burleson et al. | 128/305 |
| 4,830,000 | 5/1989 | Shutt | 128/305.1 |
| 4,842,578 | 6/1989 | Johnson et al. | 604/22 |
| 4,844,064 | 7/1989 | Thimsen et al. | 128/305 |
| 4,867,157 | 9/1989 | McGurk-Burleson et al. | 128/305 |
| 4,904,238 | 2/1990 | Williams | 604/43 |
| 5,007,917 | 4/1991 | Evans | 606/170 |

(List continued on next page.)

FOREIGN PATENT DOCUMENTS

| | | |
|---|---|---|
| 197 19 051 A | 11/1998 | (DE) . |
| 0 440 371 A1 | 8/1991 | (EP) . |
| 0 508 710 A1 | 10/1992 | (EP) . |
| 0 666 059 A2 | 8/1995 | (EP) . |
| 0 836 833 A2 | 4/1998 | (EP) . |
| 5-103790 | 4/1993 | (JP) . |

(List continued on next page.)

FOREIGN PATENT DOCUMENTS

| | | |
|---|---|---|
| 10-118084 | 3/1995 | (JP) . |
| 10-43193 | 2/1998 | (JP) . |
| 10-216138 | 8/1998 | (JP) . |
| WO 96/31307 | 10/1996 | (WO) . |
| WO 96/39956 | 12/1996 | (WO) . |
| WO 97/03617 | 2/1997 | (WO) . |
| WO 97/16118 | 5/1997 | (WO) . |
| WO 97/38635 | 10/1997 | (WO) . |
| WO 97/39685 | 10/1997 | (WO) . |

OTHER PUBLICATIONS

K. M. Stürmer, "Measurement of Intramedullary Pressue in an Animal Experiement and Propositions to Reduce the Pressure Increase," Injury 1993, Supplement 3, pp. S7–S21.

*Primary Examiner*—Gene Mancene
*Assistant Examiner*—Michael B. Priddy
(74) *Attorney, Agent, or Firm*—Pennie & Edmonds LLP

(57) ABSTRACT

A device for expedited reaming of a medullary canal and method of using the same are disclosed. The device includes a reamer head connected at the distal end of a rotatable drive shaft. The reamer head has a cutting head with a plurality of blades and flutes therebetween. Each blade has a front cutting portion. The blades can also include a side cutting portion. The disclosed method for removing material from the medullary canal of a bone includes the steps of reaming an area of the medullary canal to remove material; irrigating the material to be removed while reaming to reduce generation of heat and move removed material from the reaming area; and aspirating the removed material while reaming to create a negative intramedullary canal pressure to assist in the removal of the material.

18 Claims, 16 Drawing Sheets

U.S. PATENT DOCUMENTS

| | | | |
|---|---|---|---|
| 5,019,036 | 5/1991 | Stahl | 604/22 |
| 5,074,841 | 12/1991 | Ademovic et al. | 604/22 |
| 5,112,299 | 5/1992 | Pascaloff | 604/22 |
| 5,114,399 | 5/1992 | Kovalcheck | 604/22 |
| 5,122,134 | 6/1992 | Borzone et al. | 606/80 |
| 5,190,548 | 3/1993 | Davis | 606/80 |
| 5,217,479 | 6/1993 | Shuler | 606/180 |
| 5,224,929 | 7/1993 | Remiszewski | 604/30 |
| 5,269,785 | 12/1993 | Bonutti | 606/80 |
| 5,312,408 | 5/1994 | Brown | 606/80 |
| 5,403,317 | 4/1995 | Bonutti | 606/80 |
| 5,405,348 | 4/1995 | Anspach, Jr. et al. | 606/80 |
| 5,443,468 | 8/1995 | Johnson | 606/80 |
| 5,487,747 | 1/1996 | Stagmann et al. | 606/166 |
| 5,489,291 | 2/1996 | Wiley | 606/170 |
| 5,556,399 | 9/1996 | Huebner | 606/80 |
| 5,569,254 | 10/1996 | Carlson et al. | 606/79 |
| 5,569,284 | 10/1996 | Young et al. | 606/180 |
| 5,577,517 | 11/1996 | Bonutti | 128/898 |
| 5,685,673 | 11/1997 | Jarvis | 408/230 |
| 5,690,634 | 11/1997 | Muller et al. | 606/80 |
| 5,693,062 | 12/1997 | Stegmann et al. | 606/166 |
| 5,694,951 | 12/1997 | Bonutti | 128/898 |
| 5,720,749 | 2/1998 | Rupp | 606/79 |
| 5,759,185 | 6/1998 | Grinberg | 606/80 |
| 5,792,167 | 8/1998 | Kablik et al. | 606/180 |
| 5,913,859 | 6/1999 | Shapira | 606/80 |
| 5,913,867 | 6/1999 | Dion | 606/180 |
| 5,916,231 | 6/1999 | Bays | 606/180 |
| 5,922,003 | 7/1999 | Anctil et al. | 606/170 |
| 5,928,241 | 7/1999 | Menut et al. | 606/80 |
| 5,935,131 | 8/1999 | Bonutti | 606/80 |
| 5,947,972 | 9/1999 | Gage et al. | 606/80 |
| 5,951,561 | 9/1999 | Pepper et al. | 606/80 |
| 5,968,048 | 10/1999 | Harder | 606/80 |
| 5,971,988 | 10/1999 | Reccius et al. | 606/79 |
| 5,980,525 | 11/1999 | Bryant et al. | 606/80 |
| 6,001,112 | 12/1999 | Taylor | 606/159 |
| 6,042,593 | 3/2000 | Storz et al. | 606/159 |
| 6,053,923 | 4/2000 | Veca et al. | 606/80 |
| 6,132,448 | 10/2000 | Perez et al. | 606/180 |

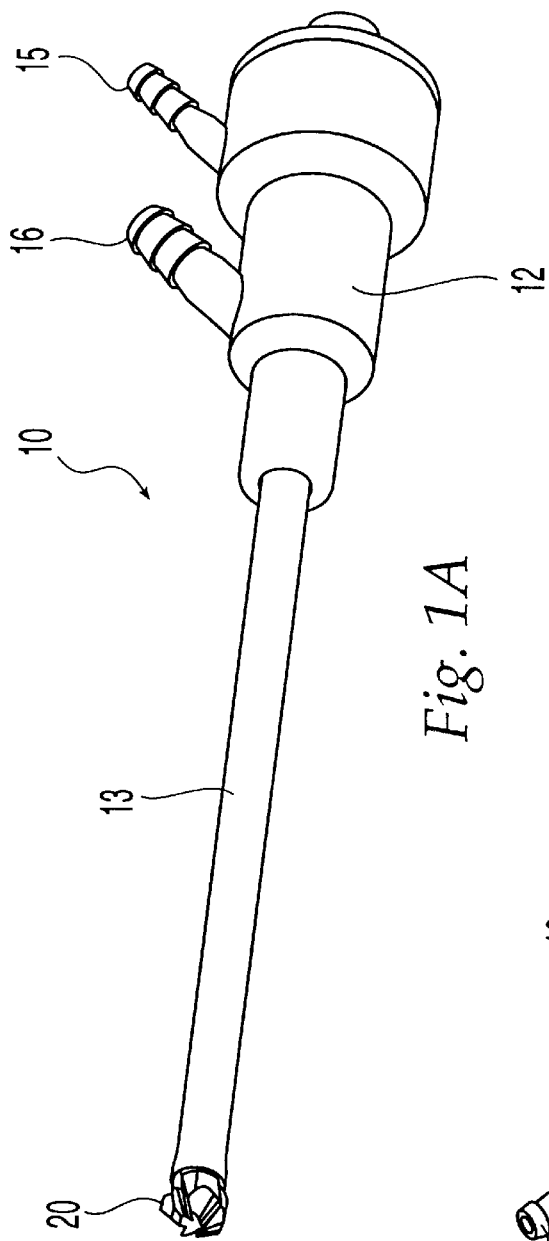
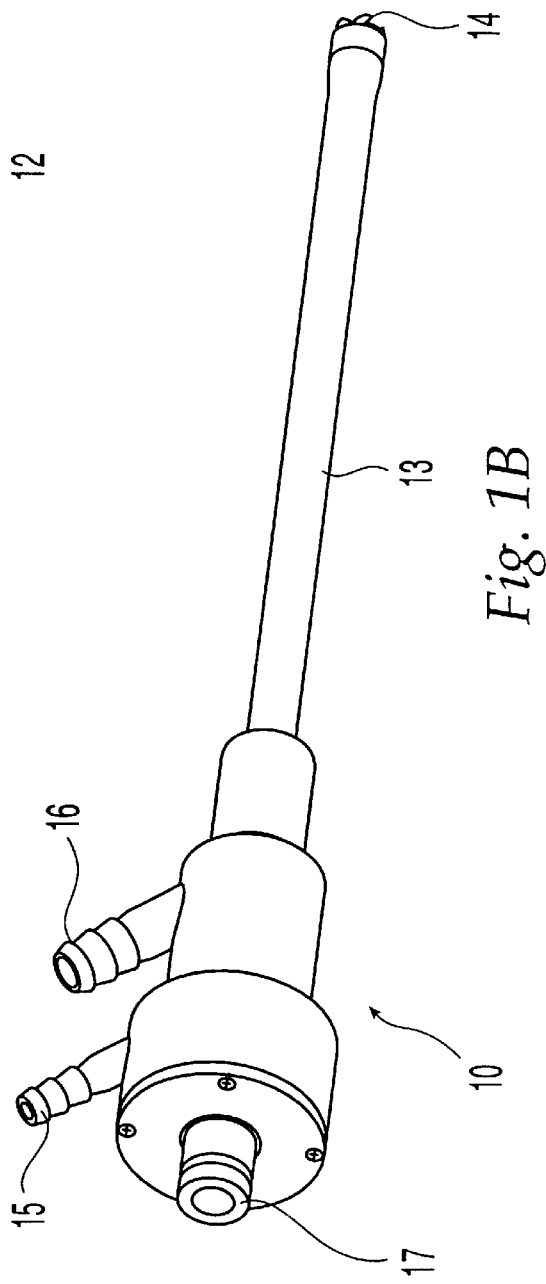

SURGICAL REAMER AND METHOD OF USING SAME

CROSS-REFERENCE TO RELATED APPLICATIONS

Priority of Provisional Application No. 60/118,485 filed Feb. 3, 1999 is claimed under 35 U.S.C. §119(e).

FIELD OF THE INVENTION

The present invention is directed to a device and method for bone tissue removal, and in particular to a device and method for expedited reaming of a medullary canal.

BACKGROUND OF THE INVENTION

A wide variety of devices for cutting and removing bone tissue are known in the air. Examples of such include those described in U.S. Pat. No. 5,269,785 issued to Bonutti, U.S. Pat. No. 4,830,000 to Shutt, and U.S. Pat. No. 5,190,548 to Davis. In general, these and similar devices utilize a rotating cutting tip similar to a drill displaced at the distal end of drive shaft. Bone cutting devices for use in reaming the medullary canal typically use a flexible drive shaft because the medullary canals of bones are seldom straight and usually will have some degree of curvature. Most reamers also have a central bore through both the reamer and the drive shaft. The central bore is intended to receive a long, small diameter guide pin or wire which is initially inserted into the medullary canal to act as a track for the advancing reamer.

Reamers are used in orthopedic surgery to prepare the medullary canals of bone for a wide variety of surgical procedures. Such procedures include total hip and knee replacement, nail insertion to stabilize a long bone fracture, an intramedullary osteotomy, and bone harvesting for grafting purposes.

From both a mechanical and a biological point of view, medullary reaming is particularly beneficial in improving the performance of implants. Specifically, reaming expands the medullary canal so that larger diameter implants can be inserted. These larger diameter implants are less likely to fail. In fact, certain fractures require over-reaming so that larger implants can be used. Without reaming, the surgeon must use a "best guess" estimate when selecting the diameter of the implant. The medical literature contains numerous case studies reporting the adverse consequences of an inaccurate estimate. Reaming provides a direct measurement of the diameter of the medullary canal, and thereby allows for the selection of an implant that precisely fills the canal. As a result, the stability of the fracture site is enhanced by achieving endosteal contact. When implants do not fill the medullary canal, load sharing between the implant and the bone is decreased. This increases the load that is transferred to the implant and promotes both implant failure and stress shielding of the bone.

Despite such benefits, negative consequences have also been associated with medullary reaming. In particular, current procedures for reaming the medullary cavity can result in an increase in both temperature and pressure. Like any process in which material is being removed, reaming causes generation of heat. Furthermore, a hydraulic pressure, which far exceeds that of blood pressure, builds up in the cavity during reaming. The reamer acts as a hydraulic piston within the bone cavity, and if the contents of the canal, which include a mixture of medullary fat, blood, blood clots, and bone debris, enter the blood stream, an embolism can result. Excessive heat has been associated with an increased incidence of aseptic necrosis of the cortex and elevated pressure has been associated with an increased risk of fat emboli. These complications are more likely to occur in patients when extenuating factors such as shock, existing lung contusion, multiple traumas, or pre-existing pulmonary impairment are present. In these situations, the preferred method of reaming would usually not be performed due to the increased risks involved.

Various devices and methods exist for reducing the intramedullary pressure build-up during reaming. For example, in prosthetic joint replacement, a distal venting hole, a large insertion hole, and a modified technique for cement insertion have all been shown to have some success ill reducing pressure, and presumably, the chance of fat embolism. Venting holes in the bone only have little effect because their diameter is typically too small and local peak values must be assumed during the passage of the reamer. Similarly, reaming the medullary cavity less does not prevent pressure increase. In fact, pressure can be high even for reamers of small diameter.

Another technique which has been used in an attempt to reduce temperature and pressure is to perform the reaming in multiple steps with increasing size of reamers with each step. As a result, reaming procedures are done slowly with the application of gentle pressure and requiring multiple passes. Usually reaming is performed in 1 mm diameter increments until the bone cortex is reached and then in 0.5 mm increments thereafter. In this regard, the reaming is carried out with less compression force and the intramedullary pressure can be easily reduced with most reaming devices utilizing this slow process. A faster reaming process utilizing fewer passes would be desirable in order to reduce operating time and medical costs.

Another disadvantage associated with current devices and methods is the reuse of reamers. Because current methods involve the use of multiple reamers of variable sizes to create one large opening in the medullary canal, reamers are usually reused in subsequent bone reaming procedures. As a result, reamers may become blunt over time and their continued use can produce greater intramedullary pressures and a greater increase in cortical temperature. Consequently, the careful attention of surgeons and operating staff to treat the reamers gently and replace them whenever necessary is trying and costly. A single use device is desirable to avoid the problems associated with the dulling of reamers which occurs with time.

Another disadvantage of current devices is due to the use of reamer designs with shallow flutes and large shafts. It has been shown that reamers with small shafts and deep flutes are more beneficial in reducing intramedullary pressure and temperature.

Thus, there exists a need for a device and method for reaming a medullary canal at an enhanced rate without increasing the risk of fat emboli and heat necrosis upon cutting and removal of bone tissue.

SUMMARY OF THE INVENTION

The present invention relates to a device for reaming a medullary canal of a bone. The device includes a rotatable drive shaft connected at the proximal end to a rotational drive element and a reamer head rotatably coupled to the distal end of the drive shaft. The reamer head has a tubular shank engaging the distal end of the drive shaft and a cutting head integral with the shank and having a plurality of blades. Flutes are located between adjacent blades. At least some and preferable all of the blades have a front cutting portion that includes at least two planar surfaces. A helical side cutting portion may be added to any or all of the blades. Preferably, there are at least five blades and each blade has at least three planar surfaces.

In one embodiment, each blade has a front cutting edge defined by the intersection between the inner blade wall and one of the planar surfaces. This front cutting edge may be oriented at an angle of approximately 30° to 45° with respect to the longitudinal axis of the tubular shank. In another embodiment, the helical side cutting portion further includes a side cutting edge defined by the intersection between the inner blade wall and the outer blade wall.

The drive shaft and reamer head each may have a cannulation. These two cannulations are aligned when the tubular shank is engaged with the drive shaft to form a center channel. One use for this channel is for receiving a guide wire that can be used to direct the device in the medullary canal.

The device may also include an aspiration tube for removing cut material generated by the reamer head. The aspiration tube has a manifold assembly at a proximal end, a reamer head retainer at a distal end, and a lumen configured and dimensioned to receive the drive shaft. Preferably, the center channel is in fluid communication with an irrigation source to provide irrigation to the cutting head. The manifold assembly may include an irrigation port connected to the irrigation source and an irrigation chamber in fluid communication with the irrigation port. The irrigation fluid travels from the irrigation chamber through an opening on the drive shaft and into the center channel. In one embodiment in which the reamer head is larger than the aspiration tube, the reamer head retainer has a substantially spherical outer profile.

The distal end of the lumen of the aspiration tube is in fluid communication with the flutes of the reamer head and the proximal end of the lumen is in fluid communication with a suction source. Preferably, the manifold assembly includes an aspiration port connected to the suction source to assist in the removal of the cut material.

The invention also relates to a method for removing tissue from a medullary canal of a bone. This method includes the steps of reaming an area of the medullary canal to remove the material; irrigating the material to be removed while reaming to reduce generation of heat and move removed material from the reaming area; and aspirating the removed material while reaming to create a negative intramedullary canal pressure to assist in the removal of the material.

The method may also include the step of inserting an implant in the medullary canal after the removal of material. Preferably, the reaming is done with a single reaming device, and the device may be guided to the appropriate location in the medullary canal using a guide wire which passes through a cannulation in the device. In another embodiment, the method includes the step of harvesting the removed tissue for use as a graft.

BRIEF DESCRIPTION OF THE DRAWINGS

Preferred features of the present invention are disclosed in the accompanying drawings, wherein similar reference characters denote similar elements throughout the several views, and wherein:

FIG. 1A is a perspective view from the distal left side of one embodiment of a reamer device according to the present invention.

FIG. 1B is a perspective view from the proximal right side of the device of FIG. 1A.

DETAILED DESCRIPTION OF THE PREFERRED EMBODIMENTS

Figure 2:
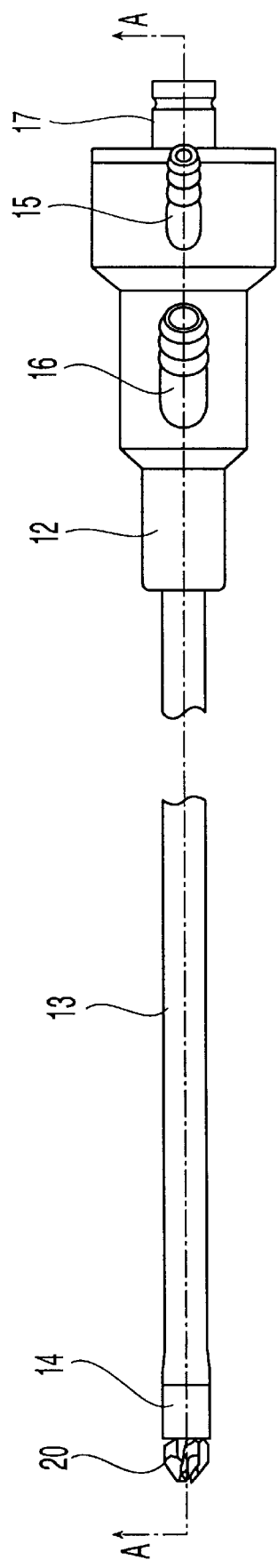
FIG. 2 is a top view of the reamer device of FIGS. 1A and 1B.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Figure 3:
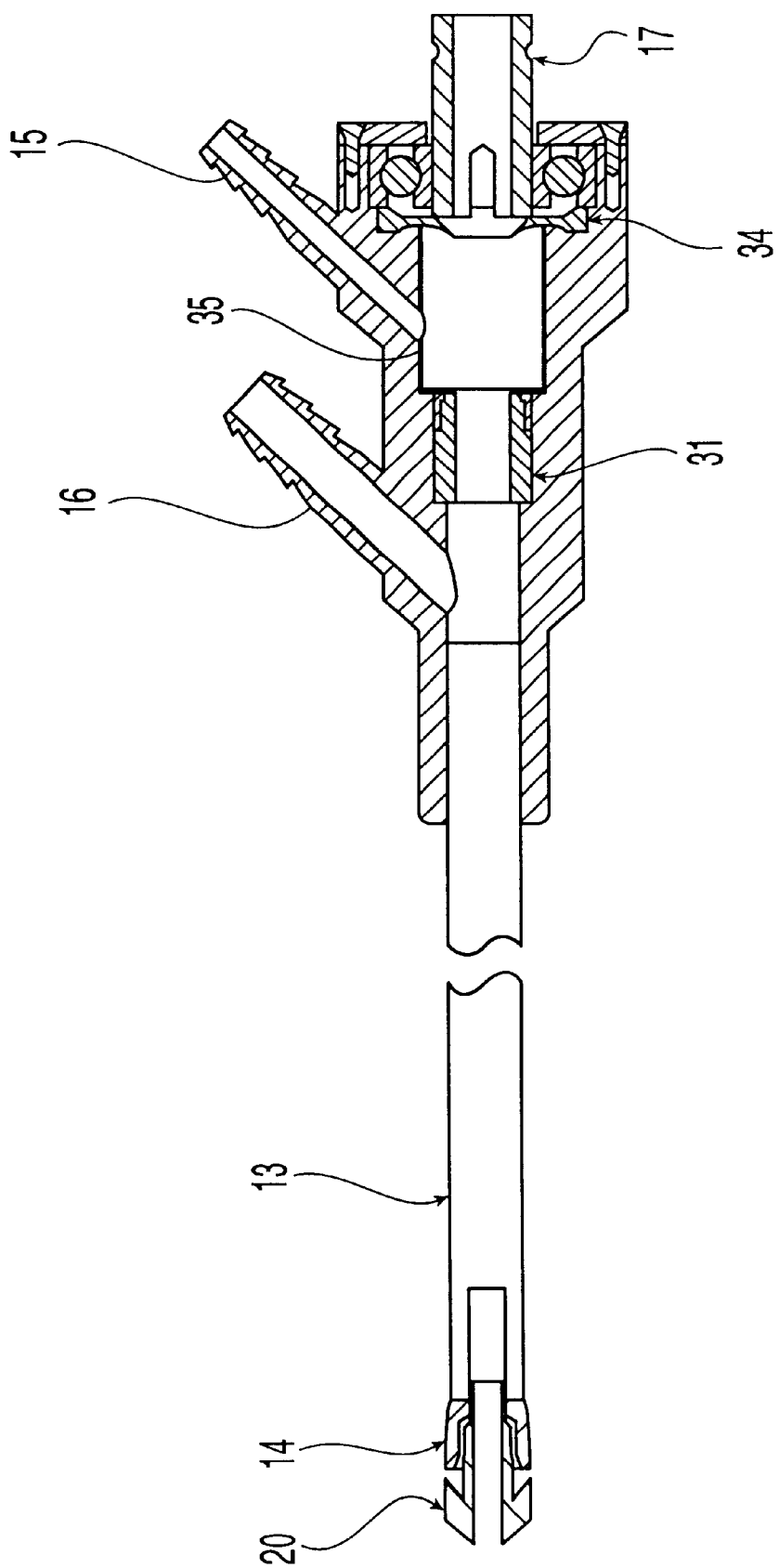
FIG. 3 is a cross-sectional view of the device taken along line A—A of FIG. 2.

Referring to FIGS. 1–3, a first embodiment of a reamer 10 according to the present invention comprises a reamer head 20 located at a distal end of reamer 10 for reaming a medullary canal, a flexible aspiration tube 13 for suction and removal of the emulsified bone and other material generated by reamer head 20, a reamer head retainer 14 for retaining reamer head 20 on aspiration tube 13 while still allowing rotation of reamer head 20 with respect to aspiration tube 13, and a manifold assembly 12 at a proximal end of reamer 10. Thus, as used in this application, the term distal designates the end or direction near reamer head 20 and toward the front of reamer 10, and the term proximal designates the end or direction near manifold assembly 12 and toward the rear of reamer 10. The term longitudinal designates an axis central to aspiration tube 13.

Aspiration tube 13 is flexible so that it can bend to accommodate curvature of the bone and is preferably made of a translucent material so that the aspirated material can be observed. Manifold assembly 12 has an irrigation port 15 and an aspiration port 16 for connecting to an irrigation source and aspiration means respectively. A drive shaft coupling 17 is located at the proximal end of manifold assembly 12. Drive shaft coupling 17 can be readily attached and detached to a drive shaft or some other means for rotating reamer head 20.

Figure 4:
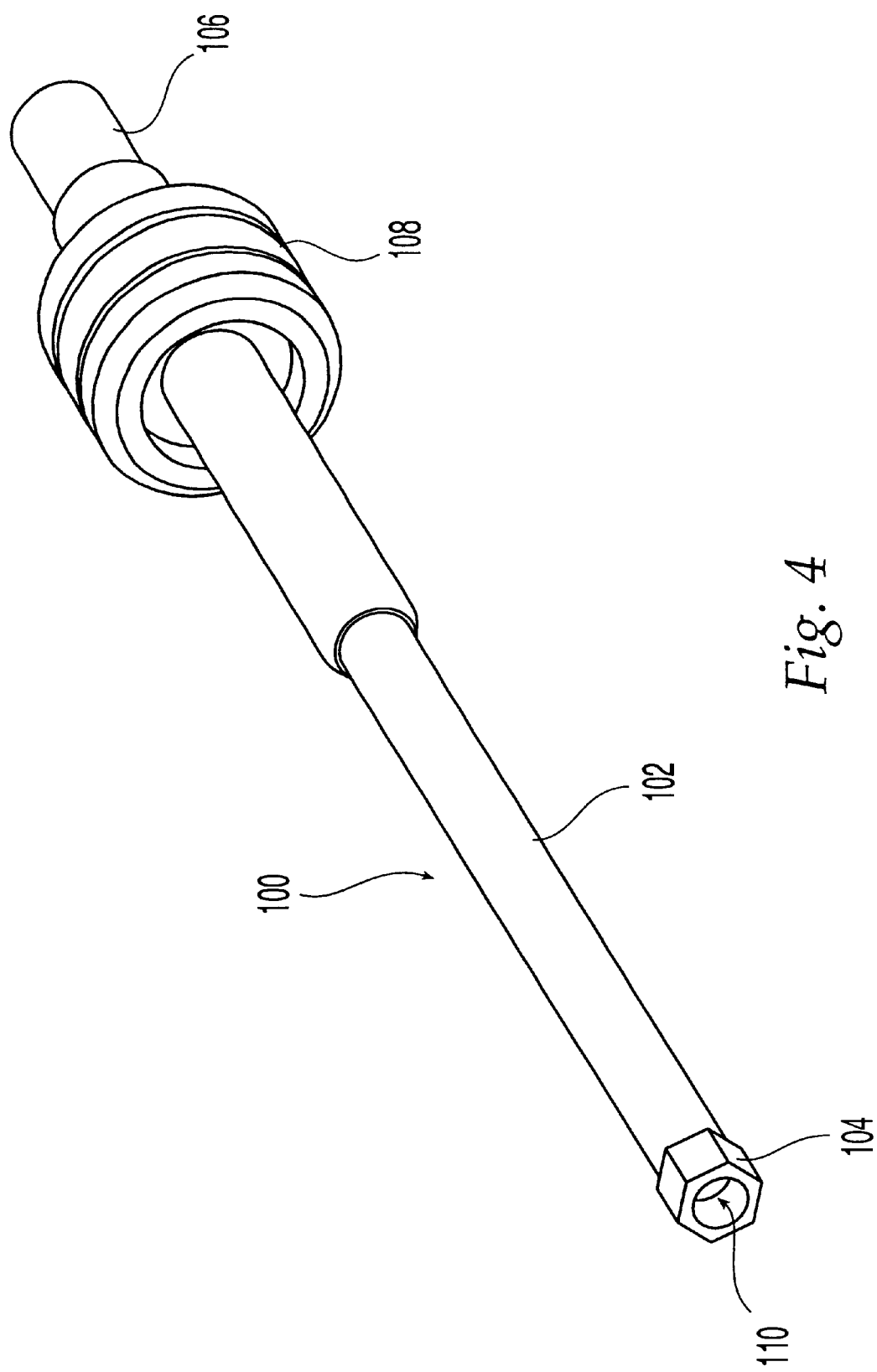
FIG. 4 is a perspective view of one embodiment of a drive shaft assembly according to the present invention.
Figure 5:
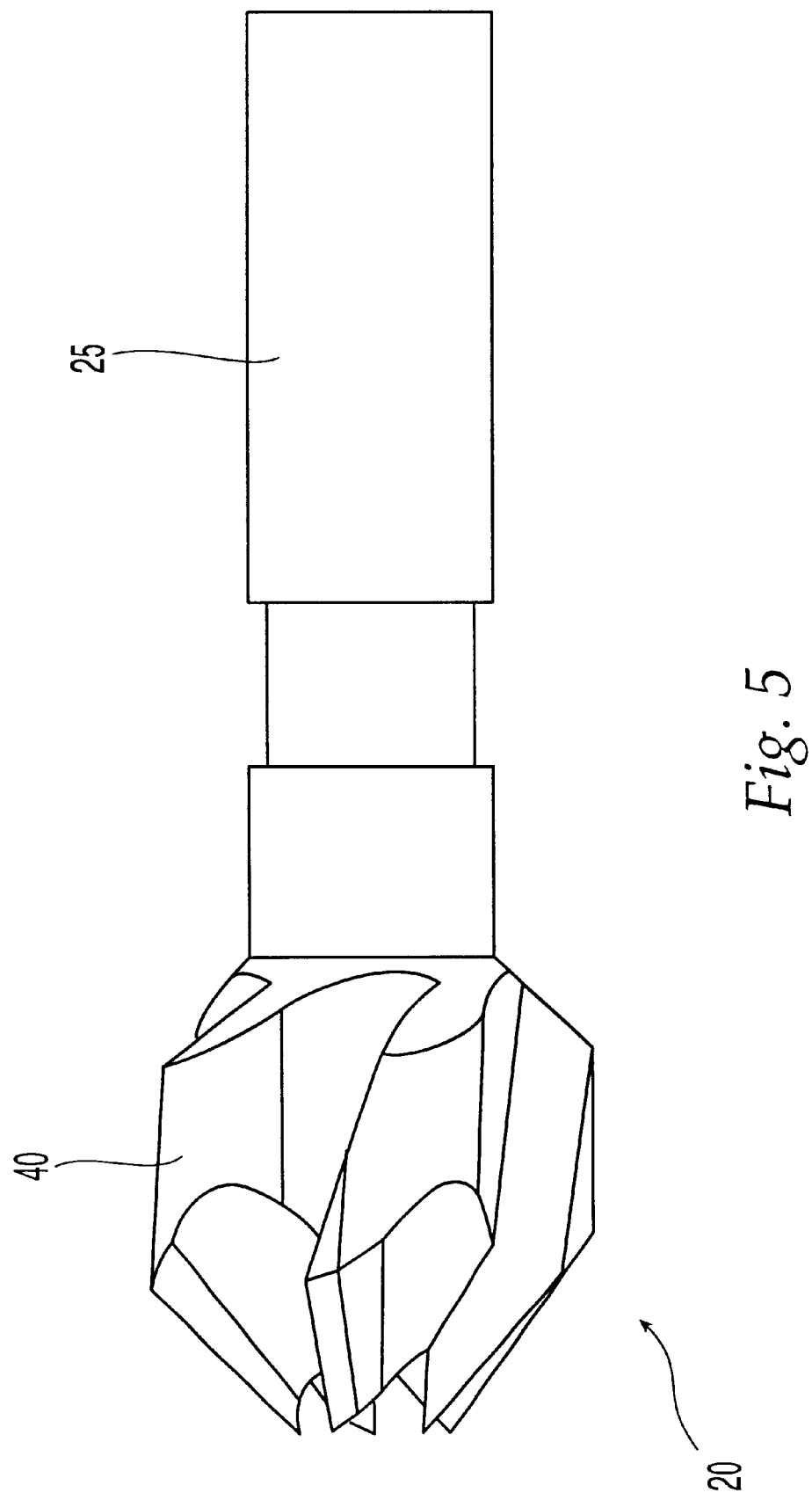
FIG. 5 is a side view of one embodiment of a reamer head according to the present invention.
Figure 6:
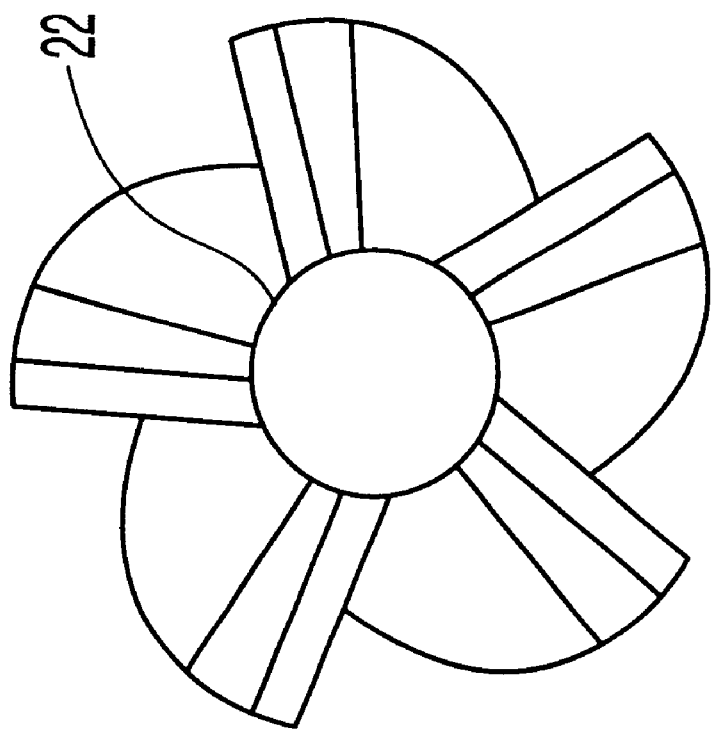
FIG. 6 is a front view of the reamer head of FIG. 5.

FIG. 4 shows a drive shaft assembly 100 that can be used with reamer 10 to rotate reamer head 20 at sufficient speeds to ream the medullary canal. The use of a drive shaft assembly 100 with reamer 10 (or any modular system in which the driving means is contained in a unit that is independent from the reamer) allows drive shaft assembly 100 to be reused with many different reamers. Such modularity is advantageous because different patients and clinical conditions will require different sized reamer heads. Furthermore, the reamer head, and not the drive means, experiences the wear and abrasion of cutting bone. Thus, reamer 10 can be a single-use, disposable item and drive shaft assembly 100 can be used for an extended period.

Drive shaft assembly 100 includes a flexible drive shaft 102 having a reamer head connector 104 on the distal end for releasably engaging reamer head 20 so that reamer head 20 rotates when flexible drive shaft 102 rotates, a power source connector 106 for connection to a source of power to initiate the rotation of drive shaft 102, and a manifold coupling 108 located between reamer head and power source connectors 104, 106 for engaging drive shaft coupling 17. Drive shaft 102 is sized to fit within the lumen of aspiration tube 13. However, as will be described in more detail later, there is sufficient space between the outer wall of drive shaft 102 and the inner wall of aspiration tube 13 to allow transport of aspirated material from reamer head 20 through aspiration tube 13 to aspiration port 16. As was the case for aspiration tube 13, drive shaft 102 is flexible to conform to any curvature of the bone being reamed. Drive shaft 102 has a cannulation 110 for accommodating a guide wire 120.

Figure 11:
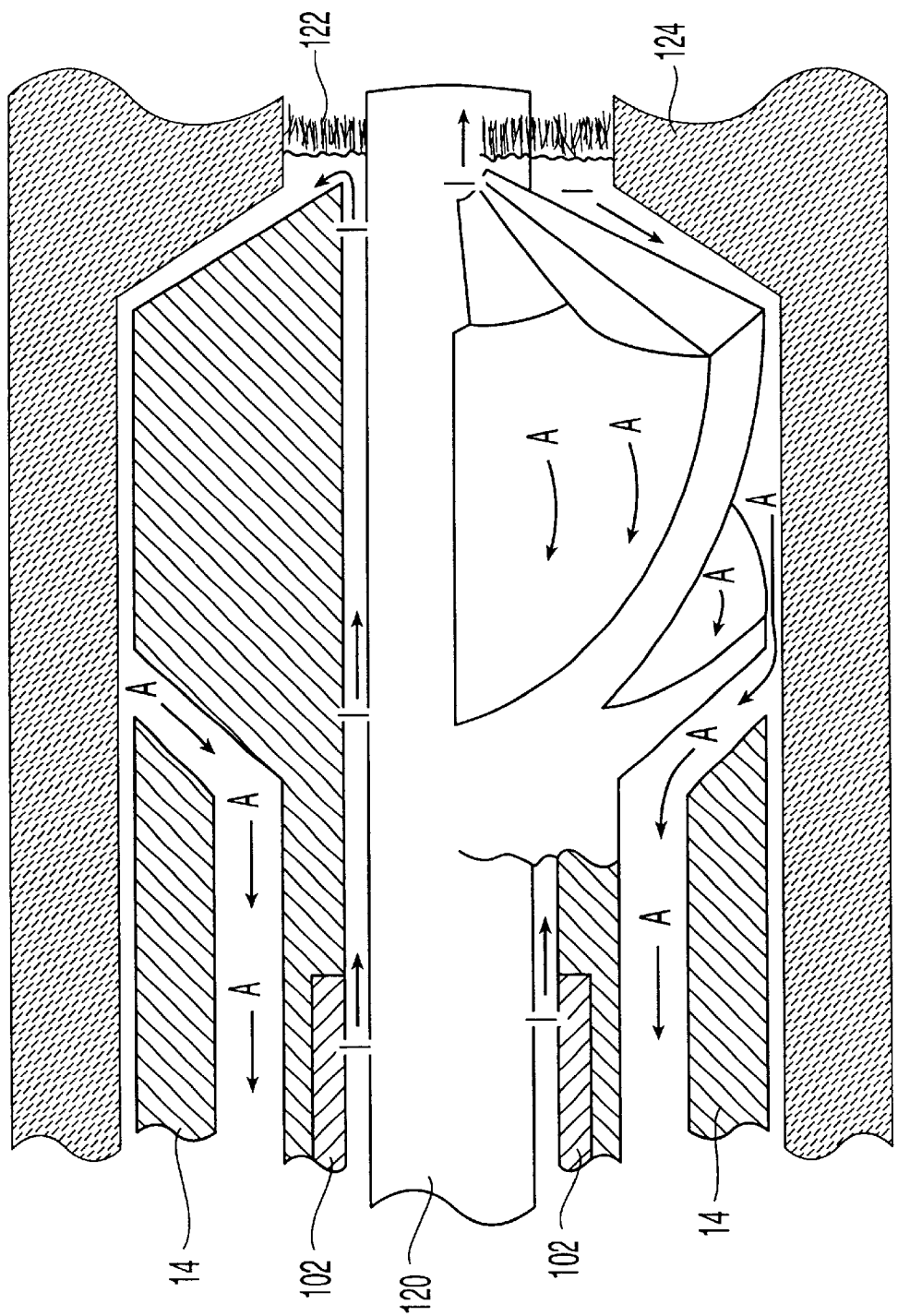
FIG. 11 is an enlarged and partially fragmented perspective and cross-sectional view of the reamer shown in FIGS. 1A and 1B.
Figure 13:
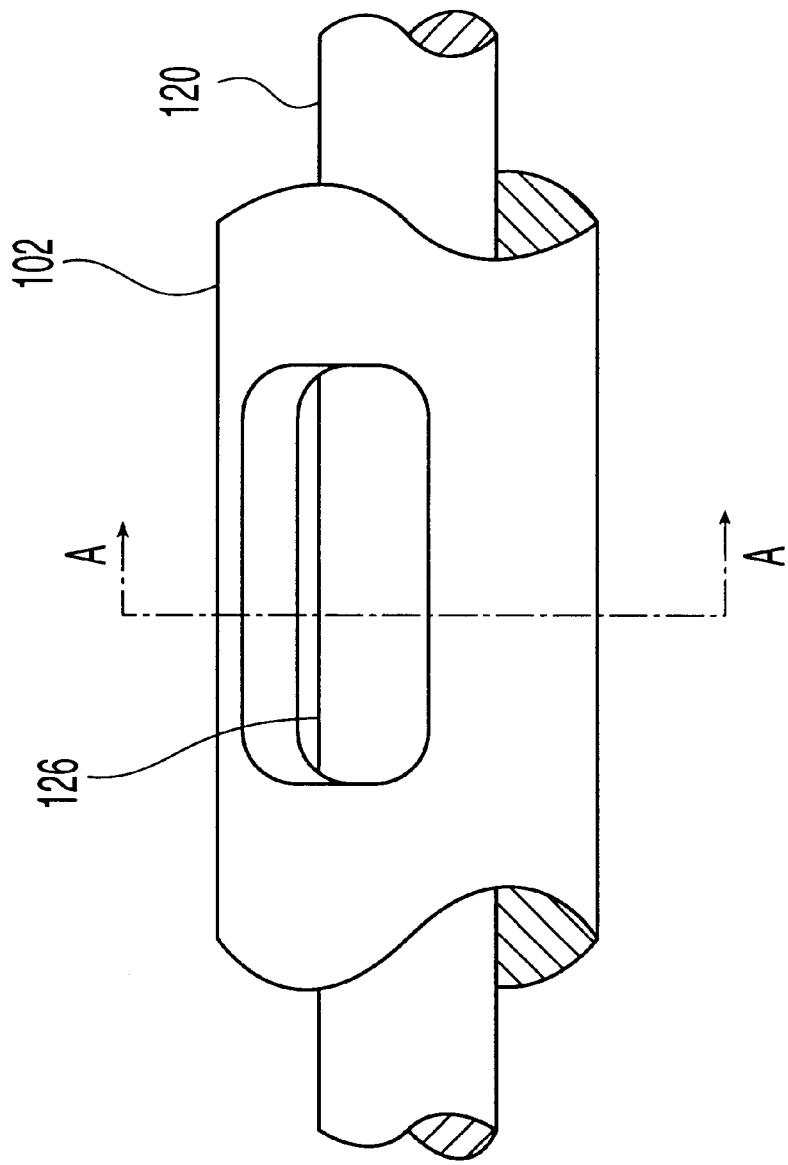
FIG. 13 is a perspective view of a portion of the drive shaft assembly of FIG. 4 with a guide wire inserted in the cannulation of the drive shaft.
Figure 14:
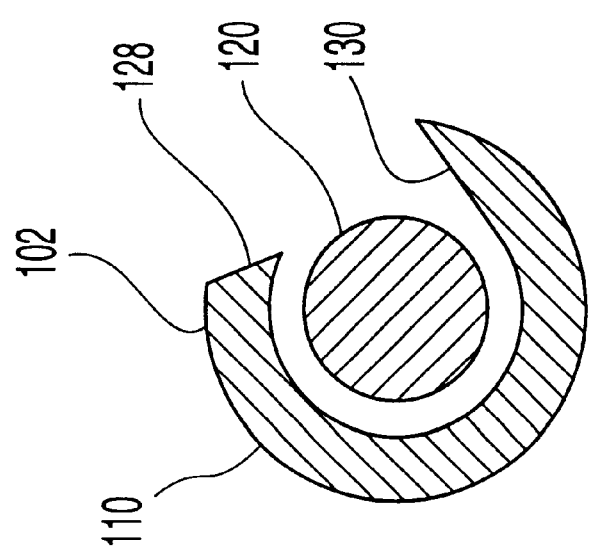
FIG. 14 is a cross-sectional view of the drive shaft assembly taken along line A—A of FIG. 13.

As seen best in FIGS. 11, 13, and 14, there is sufficient space between the outer wall of guide wire 120 and the inner wall of cannulation 110 to allow transport of an irrigation fluid from irrigation port 15 through cannulation 110 to reamer head 20. Drive shaft 102 has an opening 126 that extends from the outer surface of drive shaft 102 to cannulation 110. Opening 126 is positioned on drive shaft 102 so that when drive shaft assembly 100 is coupled to reamer device 10, opening 126 is in fluid communication with irrigation port 15 to allow irrigation to flow through cannulation 110. Opening 126 has curved walls 128, 130. Curved wall 128 bows out to have a convex profile and curved wall 130 curves inward to have a concave profile. The curvature of curved walls 128, 130 helps to draw water into cannulation 110 as drive shaft 102 rotates (which with respect to FIG. 14 is in the counter-clockwise direction).

Any suitable means for releasably joining manifold coupling 108 and drive shaft coupling 17 can be used. Preferably, a quick connect mechanism is used for rapid coupling and uncoupling. For example, manifold coupling 108 can have a spring loaded latch mechanism, such as ball bearings, which engage a groove in drive shaft coupling 17. Similarly, any suitable power source and means for securing drive shaft assembly 100 to the power source can be used. As pneumatic tools are widely used in orthopaedic surgery, the power source is preferably an air drive such as the Compact Air Drive available from Synthes (U.S.A.) of Paoli, Pa.

Referring back to FIG. 3, housed within manifold assembly 12 is a sealing element 34 and a sleeve bearing 31. Sealing means 34 and sleeve bearing 31 define an irrigation chamber 35 and provide a hermetic seal to prevent irrigation fluid from escaping irrigation chamber 35 into aspiration port 16 or out the proximal end of reamer device 10 during operation. In addition, sleeve bearing 31 prevents the aspirated emulsified material from entering irrigation chamber 35.

Figure 15:
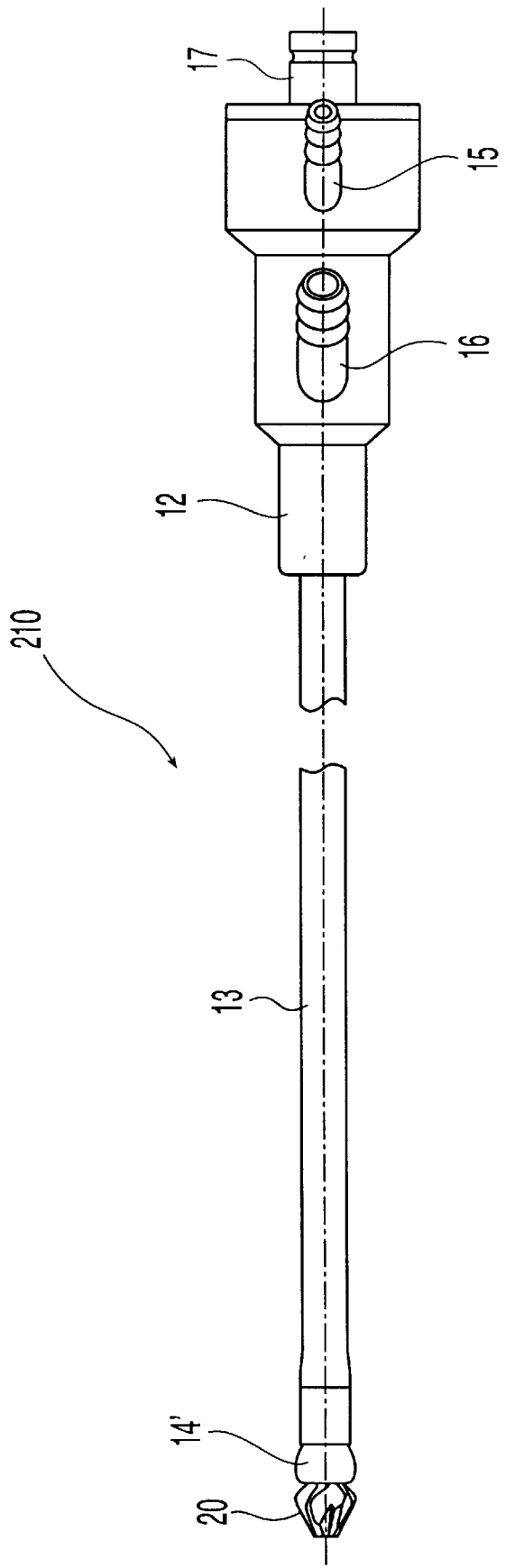
FIG. 15 is a top view of another embodiment of a reamer device according to the present invention.

Reamer head 20 is positioned coaxially within reamer head retainer 14 at the distal end of aspiration tube 13. FIG. 15 shows a reamer 210 that has a head retainer 14' with a generally spherical outer profile shape. As head retainer 14' follows reamer head 20, the shape of head retainer 14' allows head retainer 14' to glance off of the medullary canal walls should flexing occur with aspiration tube 13 with respect to drive shaft 102. Thus, head retainer 14' can move smoothly while advancing through the medullary canal, retracting after reaming, and negotiating the fracture site.

Figure 7:
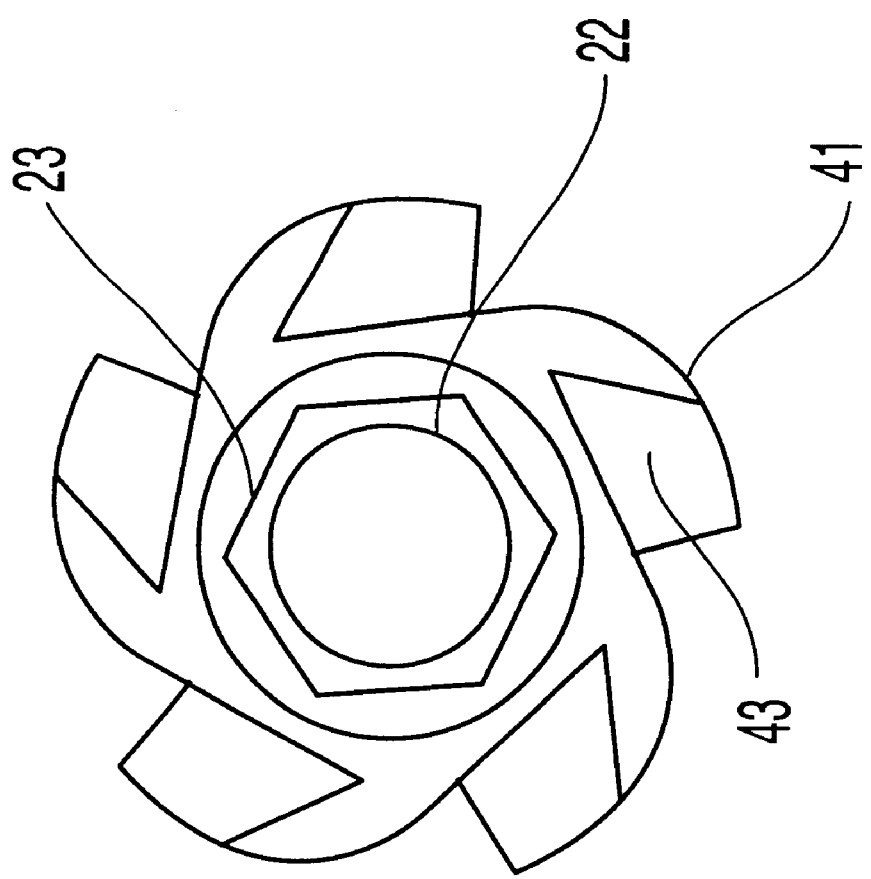
FIG. 7 is a rear view of the reamer head of FIG. 5.
Figure 8:
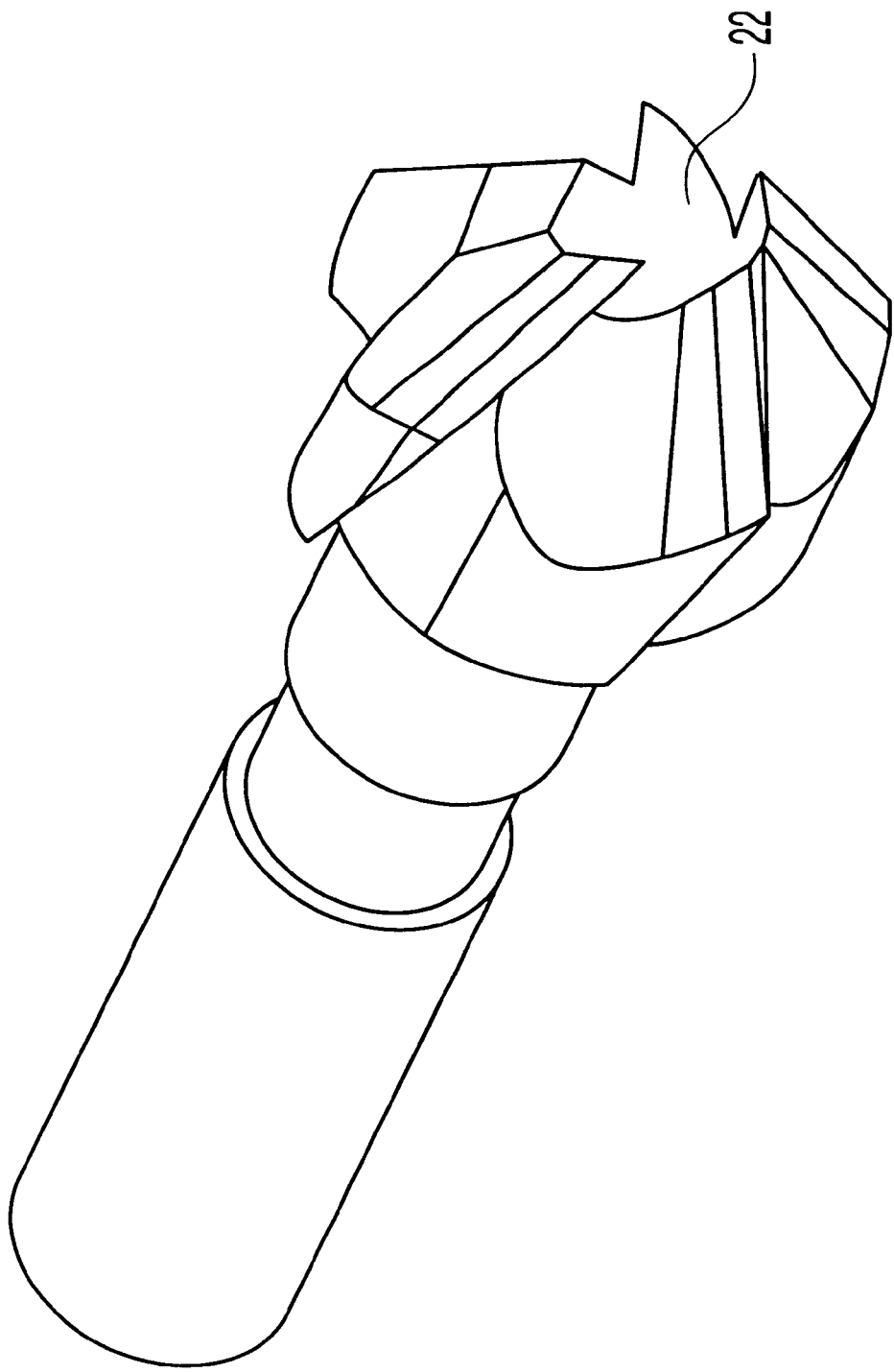
FIG. 8 is a front perspective view of the reamer head of FIG. 5.
Figure 9:
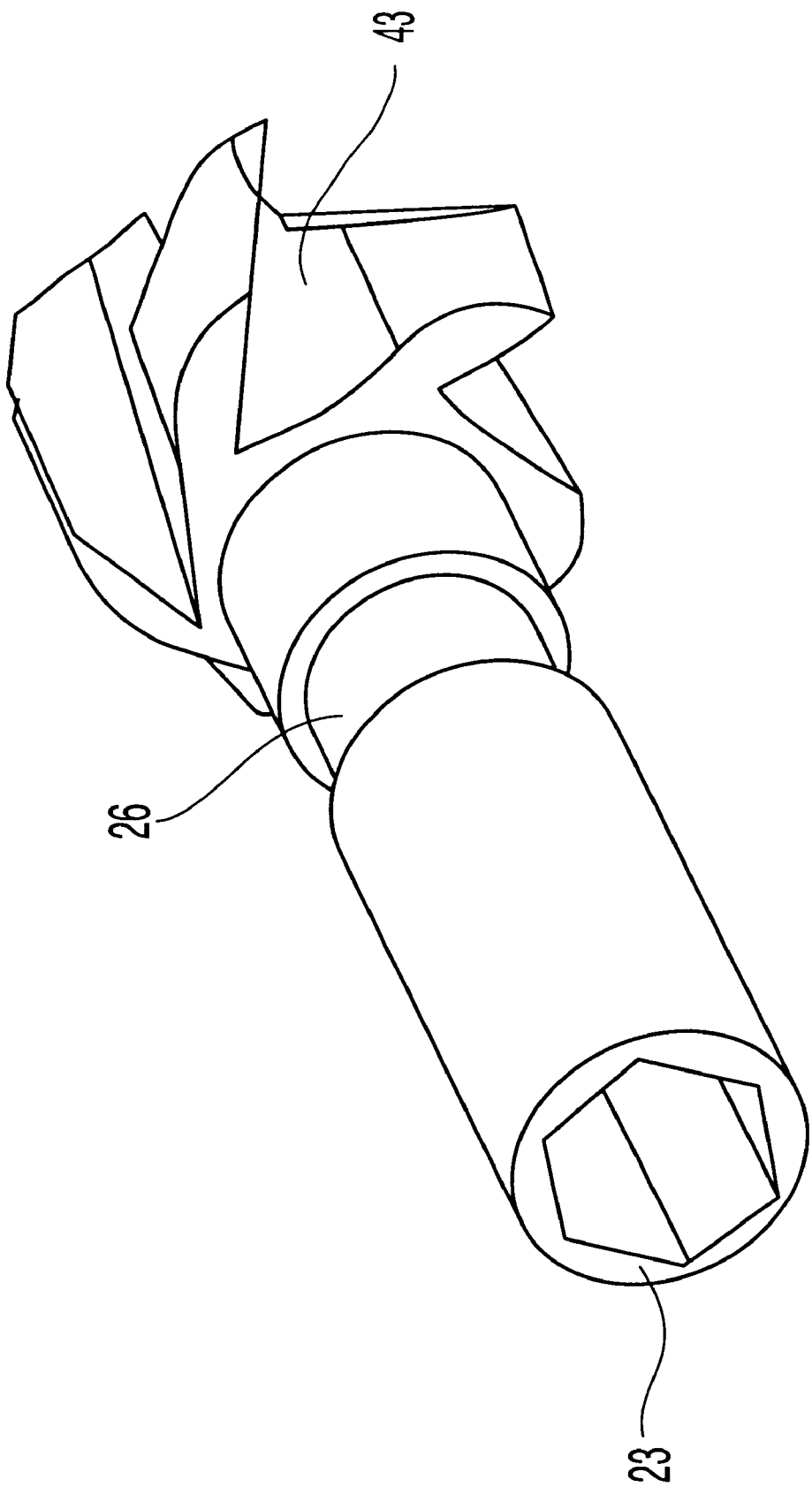
FIG. 9 is a rear perspective view of the reamer head of FIG. 5.
Figure 10:
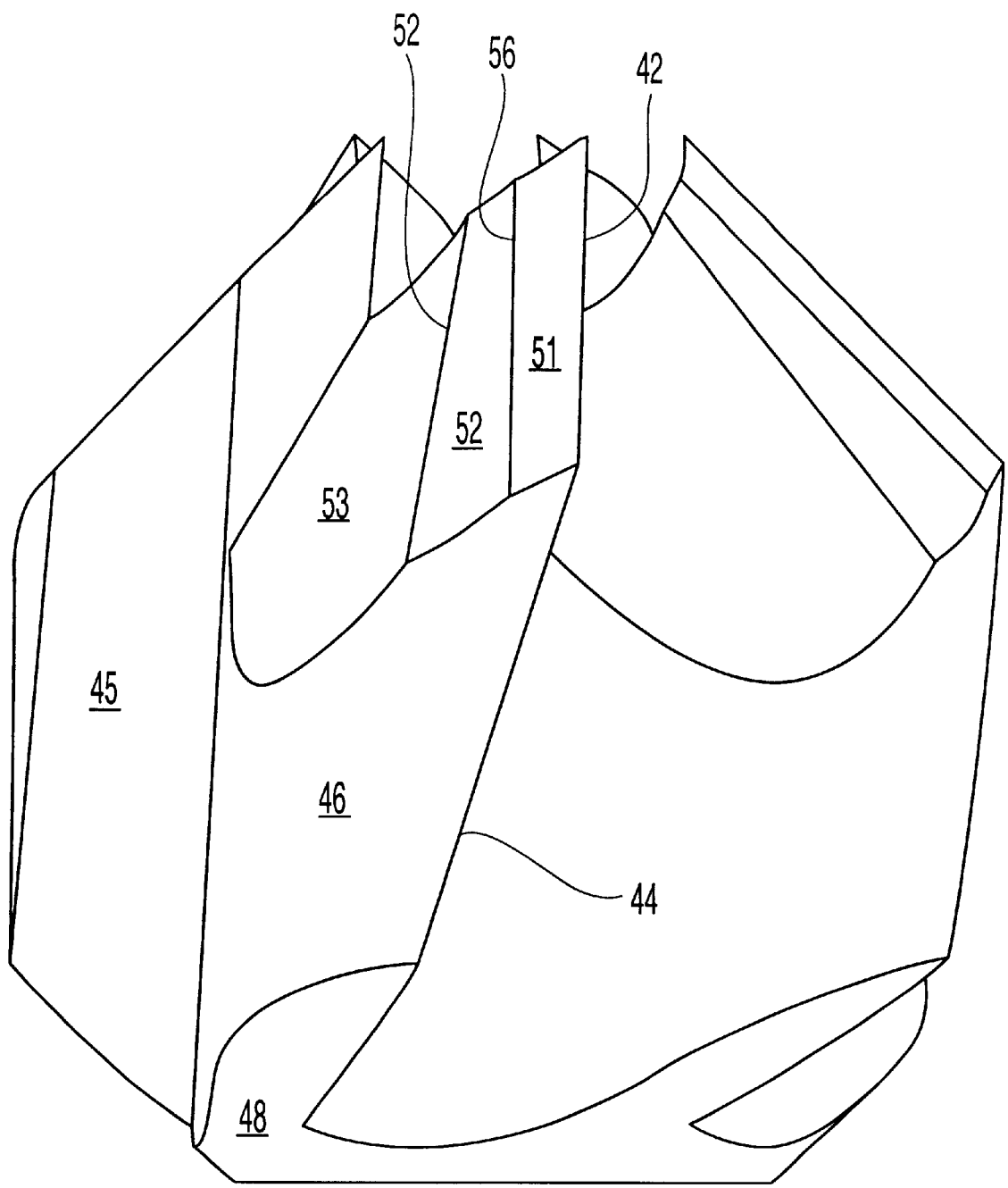
FIG. 10 is an enlarged view of the side view of FIG. 5.

Reamer head 20 is preferably made of a stainless steel, although any metallic, polymeric, ceramic, or composite material suitable for cutting bone can be used. A reamer cannulation 22 extends from the distal tip to the proximal end of reamer head 20 (FIGS. 7 and 8). Reamer cannulation 22 is aligned with cannulation 110 of drive shaft 102 so that a guide wire can extend from the proximal end of drive shaft 102 through the distal end of reamer head 20.

Although many different reamer heads can be used with reamer 10, 210, one embodiment is shown in FIGS. 5–10. As shown in these figures, reamer head 20 consists of a cutting head 40 integral with a tubular shank 25. The periphery of tubular shank 25 is cylindrical and has a retaining groove 26 indented around the periphery which accommodates an extension from the inside of reamer head retainer 14 and permits reamer head 20 to rotate while maintaining a fixed location longitudinally at the distal end of the aspiration tube 13. Tubular shank 25 has a drive shaft receptor 23 at the proximal end which is configured to accommodate reamer head connector 104 of drive shaft 102 so that reamer head 20 must rotate when drive shaft 102 rotates. Although drive shaft receptor 22 can be of any shape conforming to the exterior profile of reamer head connector 104, it is preferably a female hex feature.

Cutting head 40 of reamer head 20 has a plurality of blades 41, preferably at least five in number, extending radially outwardly from reamer cannulation 22 to form a substantially helical pattern. Correlating the number of blades to the particular blade geometry and rotation speed is advantageous in order to allow for appropriate amount of bone material to be removed while providing efficient cutting. When too many blades are used with a given blade shape, the flutes become very shallow and less bone material can be removed as a result. When an insufficient number of blades is used, the reamer head is not efficient in cutting bone tissue. In fact, the reamer head may bind or jam while cutting bone matter.

Each blade 41 has a multiple surfaced angular distal end with a straight front cutting edge 42 joined to a helical side cutting edge 44. Front cutting edge 42 is defined by the intersection between an inner blade wall 45 and a planar first lip surface 51. The angle between inner blade wall 45 and first lip surface 51 is acute. A planar second lip surface 52 intersects first lip surface 51 at an obtuse angle to form a first lip edge 56. A planar third lip surface 53 intersects second lip surface 52 at an obtuse angle to form a trailing lip edge 58. Side cutting edge 44 is defined by the intersection between inner blade wall 45 and an outer blade surface 46 and is at a constant radial distance from the longitudinal axis and extends longitudinally in a helical fashion. Outer blade surface 46 whorls radially inward from side cutting edge 44 along an arc toward an inner blade wall of an adjacent blade. The space between such adjacent blades defines a flute 43 which, during operation, functions to funnel the cut medullary canal material towards the proximal end of reamer head 20 for removal from the bone cavity through aspiration tube 13 under vacuum. Inner blade wall 45 and outer blade surface 46 extend longitudinally on cutting head 40 terminating at the proximal end in a shoulder surface 48. Shoulder surface 48 abuts tubular shank 25.

Figure 16:
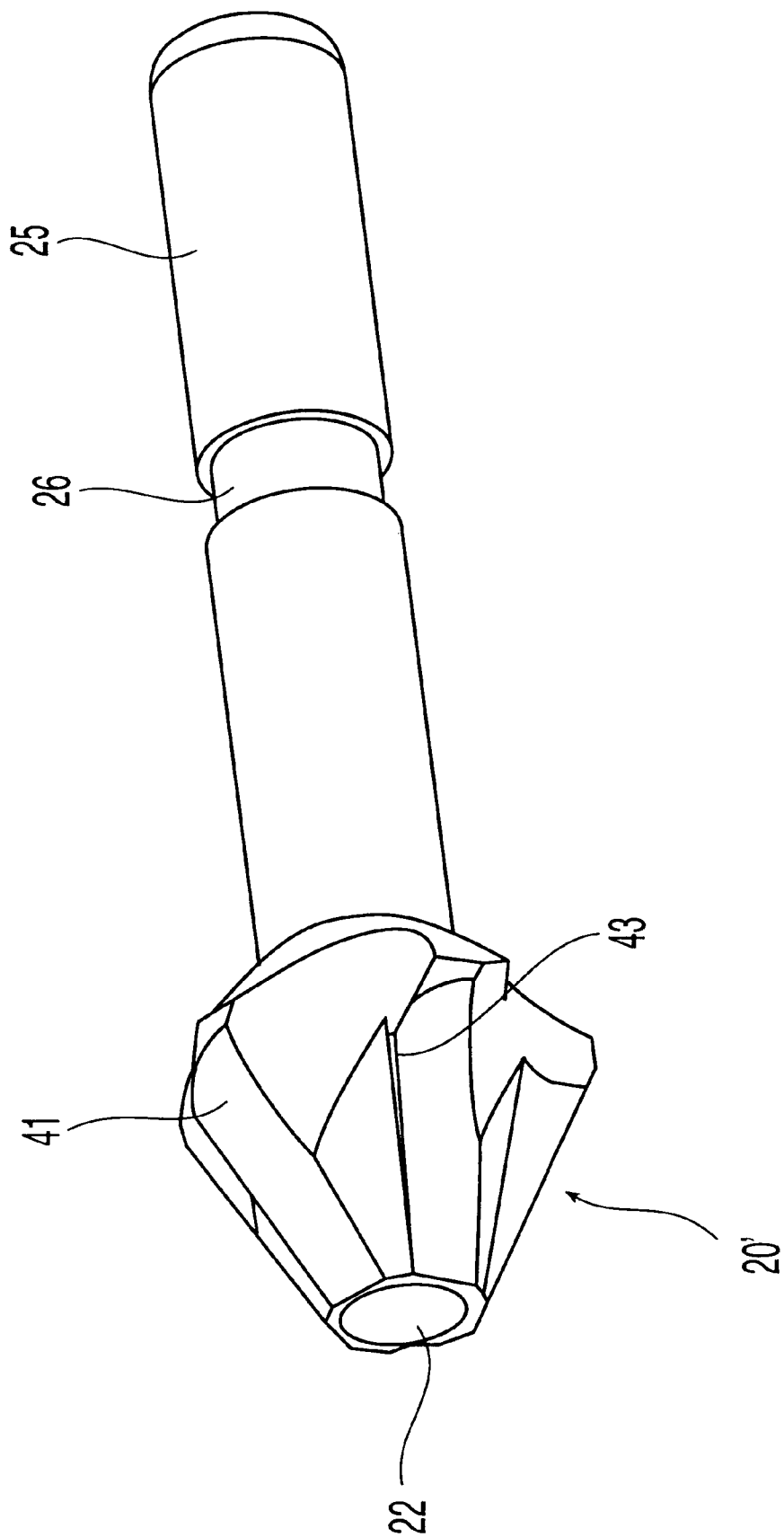
FIG. 16 is a front perspective view of another embodiment of a reamer head according to the present invention.
Figure 17:
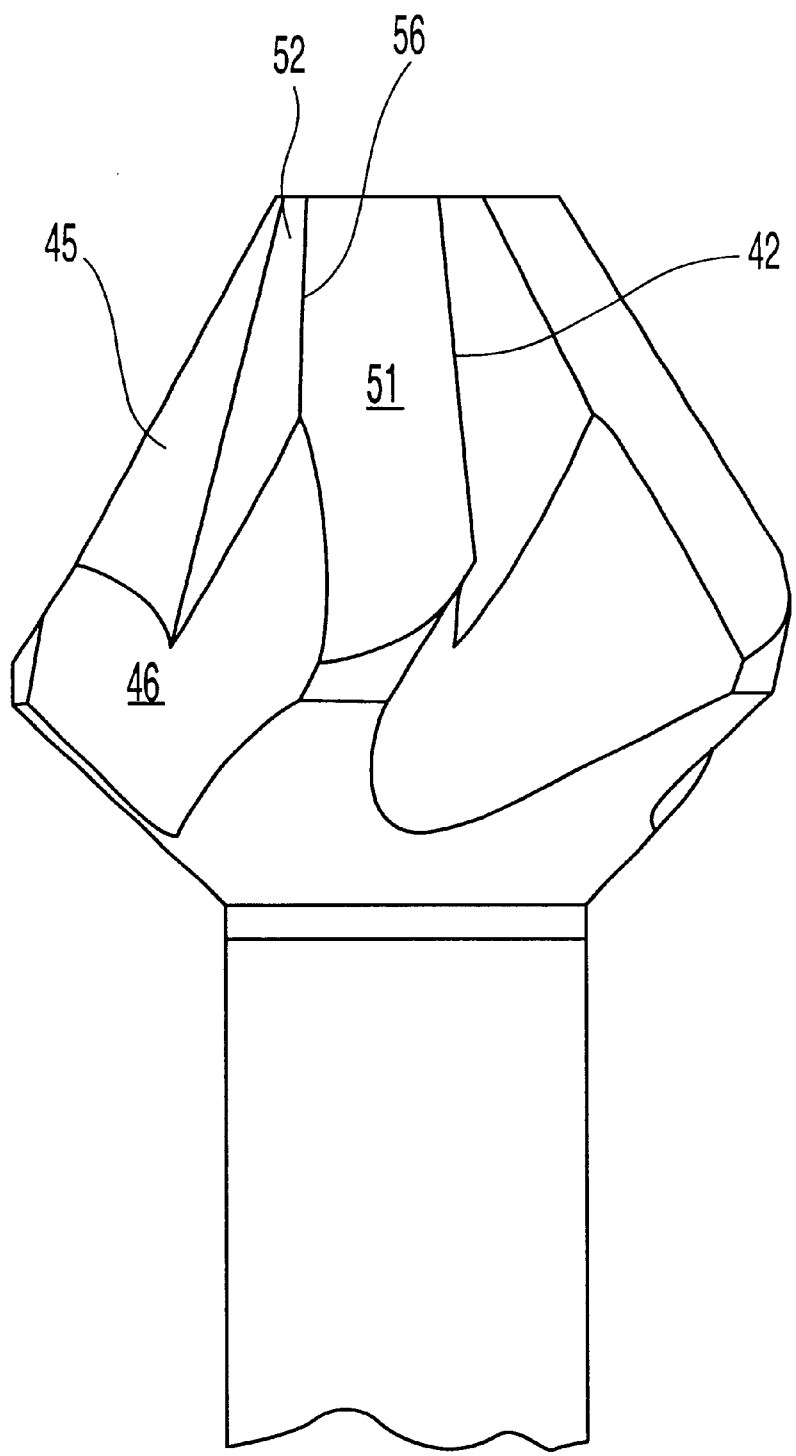
FIG. 17 is an enlarged view of the side view of the reamer head of FIG. 16.

FIGS. 16 and 17 show another embodiment of a reamer head 20' according to the present invention. Reamer head 20' does not have any side cutting edges, thereby substantially minimizing the risk of laterally reaming through the cortex of the bone. Each blade 41 has a multiple surfaced angular distal end with a straight front cutting edge 42. Front cutting edge 42 is defined by the intersection between an inner blade wall 45 and a planar first lip surface 51. The angle between inner blade wall 45 and first lip surface 51 is acute. A planar second lip surface 52 intersects first lip surface 51 at an obtuse angle to form a first lip edge 56. Outer blade surface 46 whorls radially inward along an arc toward an inner blade wall of an adjacent blade. The space between such adjacent blades defines a flute 43 which, during operation, functions to funnel the cut medullary canal material towards the proximal end of reamer head 20' for removal from the bone cavity through aspiration tube 13 under vacuum.

The use of reamer 10, which can be during open surgical, percutaneous, or any other minimally invasive procedure, will now be described referring primarily to FIG. 11. It should be noted that the use of reamer 210 is analogous to the use of reamer 10, the primary difference between reamer 10 and reamer 210 being the different geometries of head retainer 14 shown in FIG. 2 and head retainer 14' shown in FIG. 15. After the bone to be reamed has been accessed, guide wire 120 is inserted into medullary canal 122 of bone 124. The insertion of guide wire 120 is typically done using fluoroscopy to ensure proper placement of guide wire 120. Reamer 10, with an appropriate cutter (such as reamer head 20 or 20') attached and coupled with drive shaft 100, is then placed over guide wire 120 so that guide wire 120 passes completely through aspiration tube 13 and provides a track which reamer 10 follows as it reams canal 122. Preferably, reamer 10 coupled with drive shaft 100, has been connected to a driving means prior to insertion into medullary canal 122. Thus, guide wire 120 actually passes through cannulation 110 of drive shaft 102 and cannulation 22 of reamer head 20.

While reaming medullary canal 122, irrigation and aspiration are applied simultaneously. The irrigation substantially cools reamer head 20, medullary canal 122, and bone 124. A preferable irrigation source, which delivers the irrigation fluid at a sufficient rate and pressure, is a normal saline bag suspended one meter above irrigation port 15. It should also be noted that, in addition to a saline bag, any biological compatible solution and delivery system can be used as the irrigation source. The irrigation fluid passes from the irrigation source into irrigation port 15 and enters irrigation chamber 35. The irrigation fluid, traveling along the path indicated by arrows I, flows through cannulation 110 in the space between the inner wall of cannulation and guide wire 120 and out of reamer head 20.

The aspiration alleviates intramedullary pressure and helps to remove emulsified material from reamer head 20. The removal of material not only improves reaming, but also provides for the possibility of harvesting the emulsified material for grafting purposes. Suction created by an aspiration source travels along the path indicated by arrows A. Specifically, the irrigation fluid helps to channel the emulsified material generated by reamer head 20 through flutes 43 and into the space between the outer wall of drive shaft 102 and the inner wall of aspiration tube 13 to transport the emulsified material from reamer head 20 through head retainer 14, aspiration tube 13, and aspiration port 16 and into a suitable container.

A significant advantage of the system that includes reamer 10, 210, reamer head 20, and drive shaft assembly 100 is the ability to ream the medullary canal to the desired diameter in one pass, i.e. without the need to use multiple reaming heads of gradually increasing diameter until the desired reamed size is achieved. In this regard, supplying irrigation to reamer head 20 while simultaneously providing aspiration, and using a reamer head with an efficient front cutting geometry (an optionally a side cutting geometry) produces less pressure and heat than prior art reaming devices.

Figure 12:
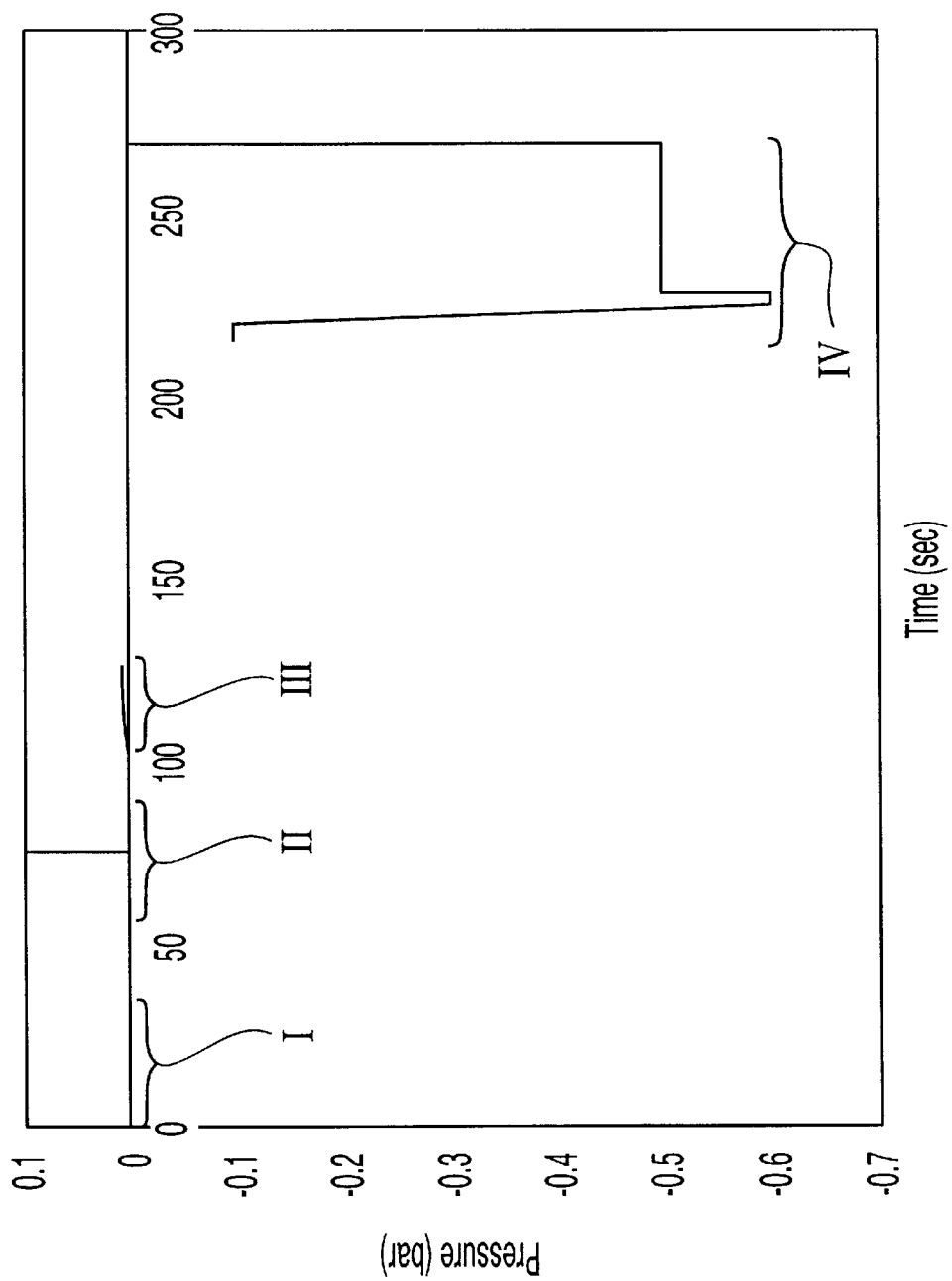
FIG. 12 shows an exemplary sample of a graph expressing a pressure-time curve of a system using the reamer of FIG. 1, the reamer head of FIG. 5, and the drive shaft assembly of FIG. 4.

FIG. 12 shows an exemplary sample of a graph expressing a pressure-time curve of the system according to the present invention in an animal model. Region I shows that no increase in pressure is induced when an access opening to the medullary canal is made. The increase in pressure in Region II results from standard techniques to gain access to the medullary canal. Region III shows that no increase in pressure is induced when the guide wire is inserted. As opposed to standard reaming process, the present invention reduces or eliminates intramedullary pressure. Specifically, the combined reaming, irrigating and aspirating functions to decrease intramedullary pressure below 100 mm Hg. In fact, as shown in Region IV, a negative intramedullary pressure is achieved with the system according to the present invention. Because the biologic threshold in the medullary canal for fat emboli and pulmonary emboli is known to be greater than or equal to 200 mm Hg, the incidence of fat and pulmonary emboli is reduced. Additionally, heat necrosis of the cortex is also eliminated due to the cooling caused by the flow of fluid during the process.

FIG. 12 shows another important advantage of the system according to the present invention. Specifically, the medullary canal reaming (Region IV) requires approximately 50 seconds. In contrast, conventional reaming in the same animal model requires approximately 500 seconds. This decrease in reaming time by a factor of ten means that reaming in clinical situations can be reduced from 30 minutes to 3 minutes. Thus, operating times (and costs) can be significantly reduced without any increased risks.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A device for reaming a medullary canal of a bone comprising:
   a rotatable drive shaft having proximal and distal ends and connected at a proximal end to a rotational drive element for causing rotation of the drive shaft; and a reamer head coupled to the distal end of the drive shaft, said reamer head comprising:
   a tubular shank having a longitudinal axis and engaging the distal end of the drive shaft; and
   a cutting head integral with the shank and having a plurality of blades and flutes therebetween for cutting and reaming of bone;
wherein each blade has inner and outer blade walls, a front cutting portion and a helical side cutting portion, with the front cutting portion comprising at least two planar surfaces and a front cutting edge defined by an intersection between the inner blade wall and one of the planar surfaces.

2. The device according to claim 1 wherein the front cutting edge is oriented at an angle from about 30° to about 45° with respect to the longitudinal axis of the tubular shank.

3. The device according to claim 1 wherein the helical side cutting portion further comprises a side cutting edge defined by an intersection between the inner blade wall and the outer blade wall.

4. The device according to claim 1 wherein the front cutting portion includes at least three planar surfaces.

5. The device of claim 1 wherein the cutting head has at least five blades.

6. The device of claim 1 wherein the drive shaft and reamer head each has a cannulation, with the drive shaft cannulation aligning with the reamer head cannulation when the tubular shank is engaged with the drive shaft to form a center channel through the device.

7. A device for reaming a medullary canal of a bone comprising:
   a rotatable drive shaft having proximal and distal ends and connected at a proximal end to a rotational drive element for causing rotation of the drive shaft;
   a reamer head coupled to the distal end of the drive shaft, said reamer head comprising:
      a tubular shank having a longitudinal axis and engaging the distal end of the drive shaft; and
      a cutting head integral with the shank and having a plurality of blades and flutes therebetween for cutting and reaming of bone; and
   an aspiration tube for removing cut material generated by the reamer head, the aspiration tube having a manifold assembly at a proximal end, a reamer head retainer at a distal end, and a lumen configured and dimensioned to receive the drive shaft,
   wherein at least some of the blades have a front cutting portion with at least two planar surfaces and
   wherein the drive shaft and reamer head each has a cannulation, with the drive shaft cannulation aligning with the reamer head cannulation when the tubular shank is engaged with the drive shaft to form a center channel through the device.

8. The device of claim 7 wherein the center channel is in fluid communication with an irrigation source to provide irrigation to the cutting head to assist in the removal of the cut material.

9. The device of claim 8 wherein:
   the manifold assembly includes an irrigation port connectable to the irrigation source and an irrigation chamber in fluid communication with the irrigation port; and
   the drive shaft has an opening extending from an outer surface of the drive shaft to the drive shaft cannulation and located within the irrigation chamber.

10. The device of claim 9 wherein the drive shaft opening has curved walls to draw irrigation into the center channel from the irrigation chamber as the drive shaft rotates.

11. The device of claim 7 wherein the lumen of the aspiration tube is in fluid communication with the plurality of flutes at the distal end and is in fluid communication with a suction source at the proximal end.

12. The device of claim 11 wherein the manifold assembly includes an aspiration port connectable to the suction source.

13. The device of claim 7 wherein the reamer head retainer has a substantially spherical outer profile.

14. A method for removing material from a medullary canal of a bone comprising the steps of:
   reaming an area of the medullary canal with the device of claim 8 to remove the material;
   irrigating the material to be removed while reaming to reduce generation of heat and move removed material from the reaming area; and
   aspirating the removed material while reaming to create a negative intramedullary canal pressure to assist in the removal of the material.

15. The method of claim 14 further comprising the step of inserting an implant in the medullary canal after the removal of material.

16. The method of claim 14 wherein the reaming is done with a single reaming device to reduce reaming time.

17. The method of claim 16 which further comprises guiding the reaming device into the medullary canal using a guide wire which passes through a cannulation in the reaming device.

18. The method of claim 14 further comprising the step of harvesting the removed material for future use.

* * * * *